US009931250B2

(12) United States Patent
Carlucci et al.

(10) Patent No.: US 9,931,250 B2
(45) Date of Patent: Apr. 3, 2018

(54) ABSORBENT PADS COMPRISING ZONES OF DIFFERENTIAL ABSORBENT CAPACITY

(71) Applicant: The Procter & Gamble Company, Cincinnati, OH (US)

(72) Inventors: Giovanni Carlucci, Chieti (IT); Andrea Peri, Kronberg (DE); Remo Bellucci, Blue Ash, OH (US); Christopher Philip Bewick-Sonntag, Cincinnati, OH (US); Tana Kirkbride, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 633 days.

(21) Appl. No.: 14/577,121

(22) Filed: Dec. 19, 2014

(65) Prior Publication Data
US 2015/0173959 A1   Jun. 25, 2015

Related U.S. Application Data

(60) Provisional application No. 61/918,883, filed on Dec. 20, 2013.

(51) Int. Cl.
| | |
|---|---|
| *A61F 13/15* | (2006.01) |
| *A61F 13/472* | (2006.01) |
| *A61F 13/536* | (2006.01) |
| *A61L 15/22* | (2006.01) |
| *A61L 15/60* | (2006.01) |
| *A61F 13/475* | (2006.01) |

(Continued)

(52) U.S. Cl.
CPC ...... *A61F 13/15203* (2013.01); *A61F 13/472* (2013.01); *A61F 13/4704* (2013.01); *A61F 13/4756* (2013.01); *A61F 13/4758* (2013.01); *A61F 13/531* (2013.01); *A61F 13/536* (2013.01); *A61L 15/22* (2013.01); *A61L 15/60* (2013.01); *A61F 2013/15406* (2013.01); *A61F 2013/15414* (2013.01); *A61F 2013/4512* (2013.01); *A61F 2013/5307* (2013.01); *A61F 2013/530554* (2013.01); *A61F 2013/530569* (2013.01)

(58) Field of Classification Search
CPC ............ A61F 13/15203; A61F 13/4704; A61F 13/4756; A61F 13/4758; A61F 13/531; A61F 13/536; A61F 2013/15406; A61F 2013/15414; A61F 2013/4512; A61F 2013/530554; A61F 2013/530569; A61F 2013/5307; A61F 13/472; A61F 15/22; A61F 15/60
USPC .......... 604/385.201, 385.24, 385.22, 385.16, 604/385.17
See application file for complete search history.

(56) References Cited

U.S. PATENT DOCUMENTS

| | | | |
|---|---|---|---|
| 2006/0189954 A1 | 8/2006 | Kudo et al. | |
| 2010/0121296 A1* | 5/2010 | Noda .................... | A61F 13/532 604/367 |

(Continued)

OTHER PUBLICATIONS

PCT International Search Report, PCT/US2014/069012, dated Mar. 19, 2015, 9 pages.

*Primary Examiner* — Jacqueline Stephens
(74) *Attorney, Agent, or Firm* — Andres E. Velarde

(57) ABSTRACT

An folded absorbent sanitary pad having a higher basis weight of superabsorbent polymer in correspondence with the folding lines which helps reducing the risk of side leakage.

9 Claims, 1 Drawing Sheet

(51) Int. Cl.
  *A61F 13/531* (2006.01)
  *A61F 13/47* (2006.01)
  *A61F 13/45* (2006.01)
  *A61F 13/53* (2006.01)

(56) References Cited

U.S. PATENT DOCUMENTS

2012/0265162 A1  10/2012  Kuramochi
2013/0265884 A1  10/2013  Brombal et al.

* cited by examiner

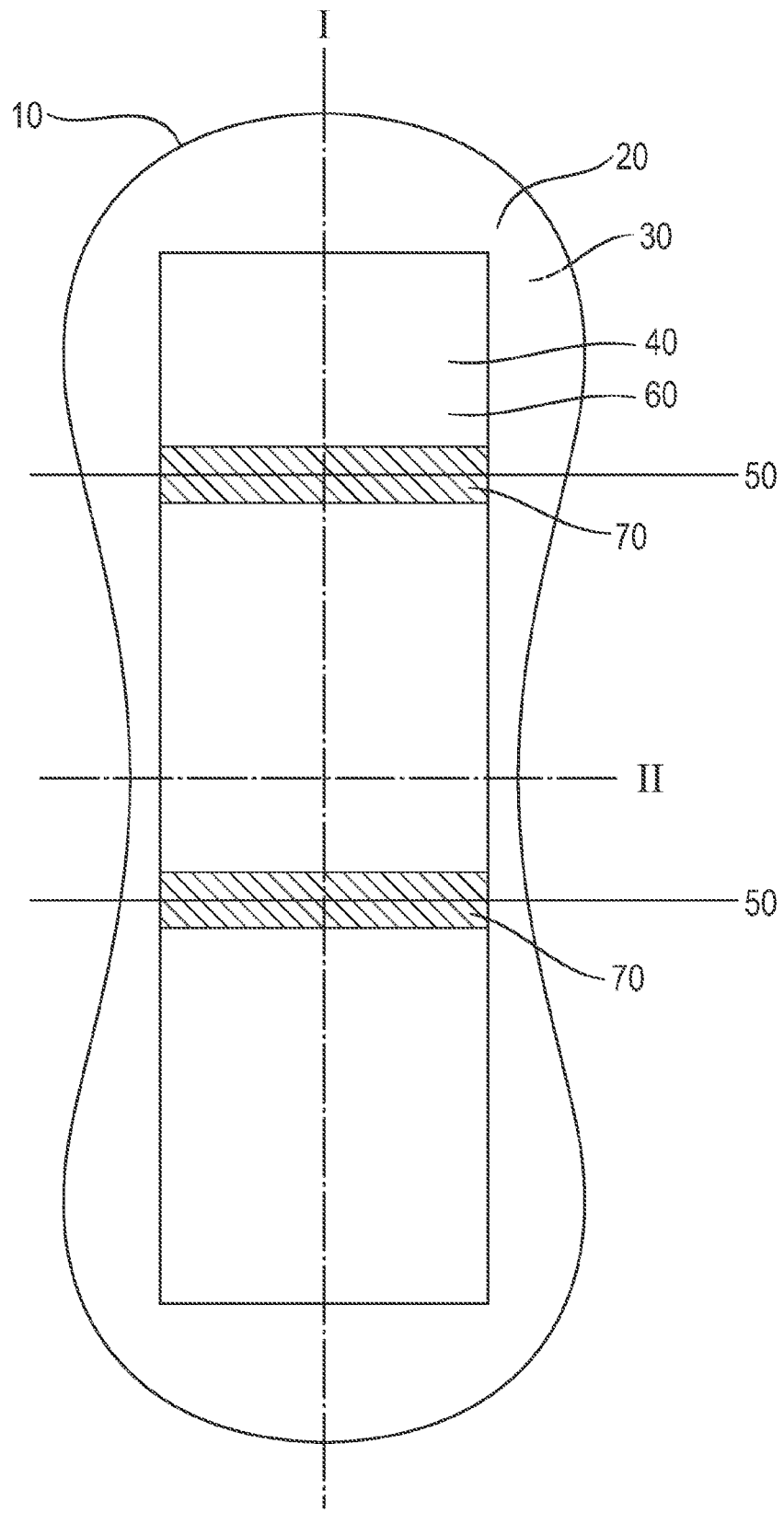

ABSORBENT PADS COMPRISING ZONES OF DIFFERENTIAL ABSORBENT CAPACITY

FIELD OF THE INVENTION

The present invention relates to absorbent pads such as sanitary napkins, pantyliners or adult incontinence pads comprising zones of differential absorbent capacity.

BACKGROUND OF THE INVENTION

Absorbent pads for absorption of body fluids such as urine, menses or blood or vaginal discharges are well known in the art, and comprise for example sanitary napkins, panty liners, as well as adult incontinence pads. These articles typically comprise a liquid pervious topsheet as wearer facing layer, a backsheet as garment facing layer and an absorbent core between topsheet and backsheet. The body fluids are acquired through the topsheet and subsequently stored in the absorbent core. The backsheet typically prevents the absorbed fluids from wetting the wearer's garment. Absorbent pads often comprise side flaps provided on the side edges of the napkin meant to be fold around the crotch edge of an undergarment during use in order to protect the undergarment from side leakages.

The absorbent core typically comprises one or more absorbent materials. Absorbent materials can be comprised typically in fibrous or particulate form, but also unitary elements formed by absorbent materials such as absorbent foam can be used.

Absorbent materials can be selected among all absorbent materials known in the art, for example natural fibres (such as for example cellulose fibres, typically wood pulp fibres), artificial fibres (such as rayon, viscose), absorbent and superabsorbent polymers (which can be used in the form of particles or fibres or foam layer or foam particles or combination thereof). Typically the absorbent core has a layered structure and is formed by one or more layers.

Absorbent pads typically comprise an adhesive on the garment facing side of the backsheet. Such adhesive is protected by a release film which can be for example a sheet of siliconized paper. Absorbent pads are commonly marketed in folded configuration wherein the article is folded 1, 2, 3, or more times around folding lines which are usually parallel to the transverse axis of the absorbent pad but can also be parallel to its longitudinal axis and/or have any other direction. In the most common configuration absorbent pads have two folding lines which are parallel to the transverse axis of the absorbent pad. Typically absorbent pads are folded and wrapped individually with a thin plastic film. Sometime the inner surface of the wrapper film is treated with a release agent such as silicone so that the film itself can also act as release film protecting the adhesive and releasing it when the wrapper of the absorbent pad is removed. Always sanitary napkins from The Procter & Gamble Company are currently marketed using this type or wrapper/release film.

The main purpose of such absorbent pads is clearly to absorb and retain body fluids and preventing as much as possible that such fluids escape from the article causing soiling of underwear and embarrassment of the user.

Modern absorbent pads are highly optimized in this respect, however the presence of folding lines can have an impact on the internal structure of the absorbent material. Absorbent pads are folded and compacted using relatively high pressures machinery in order to compact them as much as possible so that, once packaged, the articles are thin and discrete to carry in a purse. However the portions of the absorbent core in correspondence with the folding line are subject to elevated stress when folding and we have surprisingly found that their internal structure can be deeply altered so that the fluid transport and absorption properties of these portion are very different from those of the flat unfolded portions thus generating a risk of fluid leakage.

The present invention focuses on modifying the composition of the portions of the absorbent core which are in correspondence with the folding lines so that the overall properties of the core and especially the risk of leakage are reduced with respect to the same core having the same folding lines and a uniform composition. The folding line creates a densification of the core structure and (as known to the skilled person) absorbed fluids spread more quickly in core zones having a higher density. Therefore we have observed that when fluids touch the core portion in correspondence with the folding line the fluid is quickly transported along the folding line thus greatly increasing the risk that the fluid reaches the perimeter of the article and causes side soiling.

Specifically in the present invention the problem has been inventively solved by increasing the basis weight of the SAP in a small selected zone in correspondence with the folding lines of the article. It has been observed in fact that surprisingly it is sufficient to increase the basis weight of SAP in a small defined area of the absorbent core as explained in detail in the invention description below to obtain a significant improvement reducing the risk of leakage.

SUMMARY OF THE INVENTION

The present invention relates to a folded absorbent pad (10) having, in its flattened unfolded configuration a central longitudinal axis (I) and a central transversal axis (II). The pad (10) comprises:

a topsheet (20), a backsheet (30) and an absorbent core (40) disposed between topsheet (20) and backsheet (30) and one or more folding lines (50).

The absorbent core (40) comprises a storage layer (60) which comprises SAP. The storage layer, in correspondence with the one or more folding lines (50) comprises one or more folding portions (70) being defined as portions of the storage layer (60) overlapping said folding lines (50) and extending for from 3 to 20 mm on both sides of the folding lines along a direction perpendicular to said folding lines (50).

In at least one of the folding portions (70) the average basis weight of the SAP is at least 10 gsm higher than the average basis weight of SAP in the entire storage layer (60).

DETAILED DESCRIPTION OF THE INVENTION

The unit "gsm" is intended as grams per square meter.

All percentages are to be considered as weight percentages unless otherwise specified.

The term "absorbent article" is used herein in a broad sense including any article able to receive and/or absorb and/or contain and/or retain body fluids/bodily exudates such as menses, vaginal secretions, and urine. Exemplary absorbent articles in the context of the present invention are disposable hygiene absorbent articles such as feminine hygiene absorbent articles and also adult incontinence pads. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical absorbent articles according to the present invention are sanitary napkins, panty liners, absorbent pads for low or moderate incontinence or the like. Absorbent articles suitable for use in the present invention include any type of structures, from a single absorbent layer to more complex multi layer structures. Absorbent articles according to the present invention include a fluid pervious topsheet, a backsheet, which may be fluid impervious and/or may be water vapour and/or gas pervious, and an absorbent core comprised there between.

An "absorbent pad" according to the present invention is an absorbent article having a flat configuration which is intended to be used positioned inside the undergarment of the wearer between the user's body and the undergarment, being essentially centered in correspondence with the orifices which discharge the body fluid which the pad is meant to absorb (i.e. the vagina). Typical absorbent pad products which are commonly available are sanitary napkins, pantyliners and adult incontinence pads. In the case of adult incontinence the "pad" form is particularly suitable for absorbent articles dedicated to manage light to medium urinary incontinence, in particular female urinary incontinence. As known to the skilled person, more severe forms of incontinence require specific incontinence articles which when worn have the form of pants similar to baby diapers and covering also the waist and the sides of the wearer, articles of this type, having the form of pants do not require an undergarment to be kept in position. These absorbent articles are not considered as "absorbent pads" and are not part of the scope of the present invention.

The topsheet of the absorbent hygienic article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like. Topsheets may be formed by one or more layers made of the materials mentioned above, where one layer forms the outer surface of the absorbent article and one or more other layers are positioned immediately below it. The layer forming the outer surface of the article is typically a non woven layer or a formed film and it can be treated to be hydrophilic using surfactants or other means known to the person skilled in the art.

An additional layer can be optionally present between the topsheet and the absorbent core which is commonly referred to as "secondary topsheet" or "acquisition layer". This secondary topsheet is designed to acquire the fluid on a liquid-permeable topsheet and distribute it to the underlying absorbent core. To help ensure that the secondary topsheet transfers the fluid to the absorbent core, secondary topsheets are typically made from an air-laid-tissue web or a synthetic nonwoven that has sufficient capillarity to draw the fluid through the topsheet. To ensure that the fluid flow continues on to the absorbent core, the secondary topsheet is commonly designed with more permeability than the absorbent core, and less capillarity than the absorbent core.

It is desirable for the secondary topsheet to have a basis weight of less than 125 grams per square meter, more preferred for it to have a basis weight of less than 100 grams per square meter, and most preferred for it to have a basis weight of less than 80 grams per square meter. For example an effective secondary topsheet has a basis weight of 59 grams per square meter. It has a caliper thickness of 0.75 mm, a density of 0.08 grams/cubic centimeter, and a Permeability of 80 darcy.

Examples of materials and structures for secondary topsheets which are usable in the present invention are those described in WO2012040315A1.

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. In an embodiment, a microporous polyethylene or polyethylene polypropylene film can be used as backsheet. The backsheet can be formed by one or more layers and may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Such panty fastening means can be for example a layer of adhesive or mechanical means such as Velcro® or combination thereof. When an adhesive is present, typically a release paper is also present in order to protect the adhesive before use.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m2 to about 35 g/m2. However, it should be noted that other flexible liquid impervious materials may be used as the backsheet. Herein, "flexible" refers to materials which are compliant and which will readily conform to the general shape and contours of the wearer's body.

The backsheet and the topsheet can be positioned respectively adjacent the garment surface and the body surface of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

Absorbent articles of the present invention may comprise side flaps. Side flaps (known to the skilled person also as "wings" or "side panels") are disclosed in the literature and are available in the marketplace.

Generally, side flaps extend laterally from a central portion of the absorbent article and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties. In most cases the attachment means is similar or equal to the panty fastening means of the backsheet e.g a layer of adhesive.

The flaps serve at least two purposes. First, the flaps prevent exudates which otherwise would soil the edges of the wearer's panties from doing so. Second, the flaps help stabilize the napkin from shifting out of place, especially when the flaps are affixed to the underside of the panties.

Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957.

Side flaps can be separate elements which are attached to the sides of the main body of the absorbent article along its perimeter. Alternatively they can be formed by an extension of elements forming the main body of the article such as the topsheet, the backsheet or both. In some cases also other layers forming the absorbent article such as the absorbent core, or a secondary topsheet can extend to the side flaps.

The absorbent core can be any absorbent member which is generally compressible, conformable, non-irritating to the wearer's skin, and capable of absorbing and retaining body fluids. The absorbent core may be manufactured in a wide variety of sizes and shapes (e.g., rectangular, hourglass, "T" -shaped, asymmetric, etc.).

Typically the absorbent structure is rectangularly shaped, for ease of manufacturing. However, it may be differently shaped, for example there is frequently a wearer preference for an absorbent structure which is narrower at the center than at the ends, to comfortably accommodate the legs, and obviate or minimize occurrences of bunching or wadding of the core. Oval shaped core have been proposed (e.g. WO2005/084596). Further generic and specific information regarding absorbent structures can be found for example in WO0207662A1 and WO09119471.

The absorbent core can comprise a wide variety of liquid-absorbent materials commonly used in disposable absorbent articles.

Non-limiting examples of liquid-absorbent materials suitable for use in the absorbent core include comminuted wood pulp which is generally referred to as airfelt; creped cellulose wadding; chemically stiffened, modified, or cross-linked cellulose fibers; meltblown polymers including co-form; synthetic fibers including crimped polyester fibers; tissue including tissue wraps and tissue laminates; capillary channel fibers; absorbent foams; absorbent sponges; synthetic staple fibers and superabsorbent polymers (SAP).

The configuration and construction of the absorbent core may include one or more layers or structures.

In the present invention the absorbent core comprises superabsorbent polymers (SAP) and optionally cellulosic fibers (such as cellulose, rayon, viscose etc.). Other optional constituents of absorbent cores according to the present invention are bicomponent fibers and binders (such as latex) or glues such as fiberized hot melt glue which in certain embodiments, can be used to immobilize the superabsorbent polymer particles.

Other optional components of the absorbent core are the core wrap, i.e., a material, typically but not always a nonwoven material, which either partially or totally surrounds the core. Suitable core wrap materials include, but are not limited to, cellulose, hydrophilically modified non-woven materials, perforated films and combinations thereof. Other optional components of core are acquisition and/or distribution layers which are meant to distribute the fluid in the core or a fibrous "dusting" layer optionally underlying the storage layer.

In the absorbent articles of the present invention the absorbent core typically has a flat shape and can be formed by one or more distinct layers. In the present invention the term "storage layer" refers to the layer or layers of the core which comprise superabsorbent polymer (also referred to as "SAP"). In case in a given absorbent core more than one layer comprises superabsorbent polymers, the term "storage layer" is intended to include the combination of these layers (including those cases where such layers are not adjacent). E.g. in case a core is formed by two SAP containing layers sandwiching one SAP free layer, the term "storage layer" refers to the combination of the two layers comprising SAP.

The "storage layer" has the main function to store the liquids absorbed and to not release them even under moderate pressures.

Superabsorbent polymers (SAP) are known in the art and are defined herein as polymeric materials that can absorb at least 10 times their weight of an aqueous 0.9% saline solution as measured using the Centrifuge Retention Capacity test (EDANA WSP 241.2-05). Any superabsorbent polymer can be used in the present invention. Examples of superabsorbent polymers are absorbent gelling materials (AGM), and superabsorbent foam materials.

Absorbent gelling materials (AGM), are typically used in finely dispersed form, e.g. typically in particulate or fiberized form, in order to improve their absorption and retention characteristics. AGM typically comprises water insoluble, water swellable, hydrogel forming crosslinked absorbent polymers which are capable of absorbing large quantities of liquids and of retaining such absorbed liquids under moderate pressure. Absorbent gelling materials can be incorporated in absorbent articles, typically in the core structure, in different ways; for example, absorbent gelling materials in particulate form can be dispersed among the fibres of one or more of the fibrous layers comprised in the core, or rather localized in a more concentrated arrangement between fibrous layers so that one or more of the layers making up the core comprise a reduced amount of fibrous materials and/or are essentially made of SAP.

Other examples of SAP according to the present invention are porous or foamed superabsorbents such as those described in WO2010118272A1, WO2013180832A1 and WO2013180937A1 usable both as layers and in particulate form.

Absorbent articles according to the present invention may comprise any of the SAP mentioned above or a mixture thereof.

The invention will now be described in detail while referencing to FIG. 1. FIG. 1 represents a specific exemplary embodiment, but the description of the invention herein, although referencing FIG. 1 for clarity, is to be intended as completely generic and applicable to any embodiment encompassed by the claims.

The present invention relates to a folded absorbent pad (10) having, in its flattened unfolded configuration a central longitudinal axis (I) and a central transversal axis (II).

The absorbent pad (10) comprises a topsheet (20), a backsheet (30) and an absorbent core (40) disposed between topsheet (20) and backsheet (30). The pad also comprises one or more folding lines (50). The folding lines can have any direction and different folding lines can have different directions. In some embodiments (such as the one depicted) the folding lines can all be parallel to the central transversal axis (II). In other embodiments the folding lines can all be parallel to the longitudinal axis (I). Other embodiments may comprise folding lines being parallel to the central transversal axis (II) and folding lines parallel to the longitudinal axis (I).

The absorbent core (40) comprises a storage layer (60) the storage layer (60) comprises SAP and comprises, in correspondence with the one or more folding lines (50), one or more folding portions (70) which are defined as portions of the storage layer (60) overlapping the folding lines (50) and extending for from 3 to 20 mm on both sides of them along a direction perpendicular to them (50). In at least one of the folding portions (70) the average basis weight of the SAP is at least 10 gsm (or 20 gsm or 30 gsm or 40 gsm or 50 gsm) higher than the average basis weight of SAP in the entire storage layer (60).

As mentioned above the storage layer is defined as the core layer (or the combination of core layers) which comprise SAP. For the purpose of describing the present invention the storage layer is seen in the plane of the article as comprising one or more folding portions. FIG. 1, represents a specific example of an absorbent pad according to the invention and having 2 folding lines which are parallel to the transverse axis of the pad, and thus 2 folding portions (although as mentioned above, the present invention also encompass embodiments where the folding lines are 1, 2, 3, 4 or more and are oriented in any direction).

These folding portions are in general not physically distinct portions but rather different areas of the storage layer separated by boundaries which are purely geometric. In case of crossing folding lines, by definition also the folding portions will cross.

The average basis weight of the SAP in at least one of said folding portions is at least 10 gsm (or 20 gsm or 30 gsm or 40 gsm or 50 gsm) higher than the average basis weight of SAP in the entire storage layer (60).

It has been surprisingly found that by targeting an increased basis weight of SAP only in the vicinity of the folding lines it is sufficient to cause a large reduction of leakage events during product usage. This allows to greatly reducing the risk of leakage by using only a small additional amount of SAP in a precise location in correspondence with the folding lines.

In some embodiments the basis weight of SAP within the folding portion can be higher in the parts of the folding portions which are closer to the perimeter of the absorbent pad and lower in the central part.

To note, in their broadest definition, the folding portions have been defined as extending perpendicularly for from 3 to 20 mm along a direction perpendicular to said folding lines. This feature is intended to mean that, in a given absorbent article, at least one width can be identified for the folding portions, said width being comprised between 6 and 40 mm, such that the requirement that the average basis weight of the SAP in at least one of said folding portions is at least 10 gsm higher than the average basis weight of SAP in the entire storage layer is verified.

In some embodiments the folding portions are defined as extending perpendicularly for 8 mm along the longitudinal direction on both sides of respectively said first (II) and second (III) transversal axes. In these embodiments the folding portions have a width of exactly 16 mm.

In some embodiments the storage layer comprises SAP in an amount of 30% to 100% or 40 to 100%, or 50% to 100% or 60% to 100% or 70% to 100% or 80% to 100% or 90% to 100% by weight of the storage layer.

The present invention is particularly effective in absorbent articles having storage layers comprising a high wt. percentage of SAP. Storage layers having a high wt. % of SAP can be desirable in certain cases because they allow the production of absorbent articles which are very thin and flexible, for articles of this type, which are generally perceived and marketed as high quality absorbent articles, the protection from soiling is even more important while in some cases the kinetic of absorption might be slower than in conventional articles comprising also large amounts of faster absorbents such as cellulose fiber based absorbers. Cellulose fibers are normally faster in absorbing body fluids than SAP, therefore the body fluids in a storage layer having a high % of SAP and a lower amount of cellulose fibers may spread over a larger area of the article before being locked, so that the high basis weight portions of the present invention are particularly useful in preventing fluid escape in an article having a storage layer with high % of SAP.

Nevertheless the present invention is beneficial in any type of absorbent article comprising SAP with any core constructions. Core constructions which can be used in the present invention are all core constructions known in the art for absorbent pads which comprise SAP.

A traditional core construction is the so-called laminate core construction wherein a layer of AGM particles is sandwiched between two fibrous layers typically containing cellulose fibers. This construction is simple and economical but suitable especially for low capacity cores.

The most commonly used storage layers in absorbent pads are air laid nonwovens comprising cellulose fibers and SAP particles or fibers. Suitable basis weights are commonly comprised between 50 and 500 gsm. Optionally other materials such as binders and bicomponent fibers are present.

Certain air laid cores are provided with anisotropic properties in the vertical direction for fast acquisition of the fluid in the vertical direction, i.e. towards the bottom of the core. This is generally achieved by providing a unitary core having a gradient of density or capillarity (normally both) in the vertical direction, this construction is known to skilled persons as "gradient core". Gradient core materials (herein "gradient core") are designed to quickly absorb fluid from the top of the core's surface to its bottom and then distribute in the horizontal plane direction. This is usually achieved by an unitary multistratum construction which is anisotropic in the vertical direction for fast fluid acquisition. The material stratum density and the average pore size decrease from top to the bottom of the core to drive the bodily fluid to the bottom of the core.

The word "unitary" as used herein refers to a single structure, which despite potential internal variations of physical and/or chemical characteristics is provided such that it cannot be separated into individual layers. Absorbent structures made from a number of layers, which are joined to each other by macroscopic mechanical or adhesive means are not considered unitary since they are formed from individual layers that, albeit sometimes with difficulty, can be separated from each other again.

Examples of gradient cores can be found in the following exemplary patent documents: WO03/090656A1, US2002/007169, WO00/74620A1.

This type of gradient core may be preferably free of binder material, except for the bi-component fibers in the core layers and the surface binder on the garment facing surface of the core.

A suitable gradient core construction may comprise:
a first outermost layer forming said wearer facing surface, which is provided from a mixture of bi-component fibers and cellulose or viscose fibers, preferably non-softened cellulose fibers, and said first layer has a weight fraction of the overall core construction of 10%-30%,
a second outermost layer forming the garment facing surface of the core, the second layer being provided by softener treated cellulose fibers having a weight fraction of the overall core of 30%-50%, and a surface binder, preferably a latex, on said garment facing surface of said core in an amount of 0%-2% by weight of said core, and
at least one inner layer, sandwiched between said first and said second layer, the inner layer comprising non-softened cellulose fibers, optionally bi-component fibers, and further comprising super absorbent material, the inner layer having a weight fraction of the overall core of 30%-50%.

Another core construction which is known to the skilled person is the so called "airfelt free" construction. In this construction the core comprises a non woven layer which acts as a substrate for a storage layer which is predominantly made or consists essentially of SAP particles or fibers, these particles or fibers are typically immobilized by a hot melt glue which is fiberized. Often another nonwoven layer is used as top layer (so that the storage layer is sandwiched between a substrate nonwoven and a top layer nonwoven) or another structure formed by substrate, storage layer and fiberized glue is applied face to face to the first structure so that the two storage layers are in contact. Airfelt free cores are known in the art are described in a number of patent publications such as EP2022452A1, EP2067457A1, EP2338451A1, EP2453859A1.

Conventionally AGM particles are used as SAP in all core constructions, however also AGM fibers and porous superabsorbent particles such as those as described in WO2010118272A1 can be used.

Alternatively or in combination, a layer of superabsorbent foam can be used in an absorbent core. Such layer can be used as such and can constitute the entire storage layer or can be combined with other layers such as those mentioned above for the various suitable core constructions.

Superabsorbent foams can also be used as superabsorbent material in comminuted or in particulate form in a manner similar to that how AGM particles are used.

The absorbent pad may also include such other features as are known in the art including, but not limited to, lotions, acquisition layers, distribution layers, wetness indicators, sensors, elastic elements and the like.

According to the present invention, the absorbent article can be in the form of a pad, and thus typically a sanitary napkin, a pantiliner, or a pad for low or moderate adult incontinence.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A folded absorbent pad having, in its flattened unfolded configuration a central longitudinal axis and a central transversal axis said pad comprising:
   a topsheet, a backsheet and an absorbent core disposed between said topsheet and backsheet,
   one or more folding lines
   said absorbent core comprising a storage layer said storage layer comprising SAP and comprising, in correspondence with the one or more folding lines, one or more folding portions
   said folding portions being defined as portions of the storage layer overlapping said folding lines and extending for from 3 to 20 mm on both sides of said folding lines along a direction perpendicular to said folding lines wherein in at least one of said folding portions the average basis weight of the SAP is at least 10 gsm higher than the average basis weight of SAP in the entire storage layer and wherein the at least one of said folding portions having at least 10 gsm higher SAP than the average basis weight extends the entire width of the absorbent core.

2. The absorbent pad of claim 1 wherein said folding portions are defined as portions of the storage layer overlapping said folding lines and extending for 8 mm on both sides of said folding lines along a direction perpendicular to said folding lines.

3. The absorbent pad of claim 1 wherein at least one of said folding lines is parallel to said central longitudinal axis.

4. The absorbent pad of claim 1, wherein at least one of said folding lines is parallel to said central transversal axis.

5. The absorbent pad of claim 1 wherein said storage layer comprises 50-100% wt of SAP.

6. The absorbent pad of claim 5 wherein said storage layer is a layer formed predominantly by SAP and a layer of hot melt glue in fiberized form.

7. The absorbent pad of claim 1 wherein said storage layer is an air laid layer comprising fibers and SAP.

8. The absorbent pad of claim 1 wherein said SAP comprises a layer of superabsorbent foam.

9. The absorbent pad of claim 1, wherein the absorbent pad has two folding portions and wherein both folding portions have an average basis weight of the SAP is at least 10 gsm higher than the average basis weight of SAP in the entire storage layer.

* * * * *